(12) United States Patent
Popescu (10) Patent No.: US 7,486,763 B2
(45) Date of Patent: Feb. 3, 2009

(54) X RAY COMPUTER TOMOGRAPH AND METHOD FOR OPERATING AN X RAY COMPUTER TOMOGRAPH

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 48 days.

(21) Appl. No.: 11/657,668

(22) Filed: Jan. 25, 2007

(65) Prior Publication Data

US 2007/0189438 A1 Aug. 16, 2007

(30) Foreign Application Priority Data

Jan. 26, 2006 (DE) .................. 10 2006 003 829

(51) Int. Cl.
*A61B 6/00* (2006.01)

(52) U.S. Cl. ............................. 378/15; 378/4

(58) Field of Classification Search ............... 378/4–20
See application file for complete search history.

(56) References Cited

U.S. PATENT DOCUMENTS

| | | | |
|---|---|---|---|
| 5,247,566 A | | 9/1993 | Hiramatsu |
| 5,400,378 A | | 3/1995 | Toth |
| 5,412,702 A | | 5/1995 | Sata |
| 5,598,453 A | * | 1/1997 | Baba et al. .................. 378/146 |
| 6,292,527 B1 | | 9/2001 | Guendel |
| 6,393,090 B1 | | 5/2002 | Hsieh et al. |
| 6,442,235 B2 | * | 8/2002 | Koppe et al. .................. 378/62 |
| 6,501,819 B2 | * | 12/2002 | Unger et al. .................. 378/5 |
| 7,031,425 B2 | | 4/2006 | Hsieh et al. |
| 2005/0058249 A1 | | 3/2005 | Wolf et al. |

FOREIGN PATENT DOCUMENTS

| | | |
|---|---|---|
| DE | 41 03 588 C1 | 5/1992 |
| DE | 199 25 395 A1 | 12/2000 |
| DE | 103 52 645 A1 | 9/2004 |
| DE | 10 2004 043 859 A1 | 4/2005 |
| EP | 0 531 993 B1 | 9/1992 |

OTHER PUBLICATIONS

Dobbins III PhD, James T., Chest Radiography, Pt. 3 : Chest Tomosymthesis, http://www.imagingeconomics.com/library/tools/printengine.asp?printArticleID=200505-05, 2003.
Dobbins III, James T. ,Digital x-ray tomosynthesis: current state of the art and clinical potential, Phys. Med. Biol. 48 (2993) R65-R106.

* cited by examiner

*Primary Examiner*—Hoon Song
(74) *Attorney, Agent, or Firm*—Harness, Dickey & Pierce, P.L.C.

(57) ABSTRACT

A method for producing a first shadow image with the aid of an X ray computer tomograph at a prescribed first angular position is disclosed. In order to reduce the applied dose, in at least one embodiment the X ray source is operated in a pulsed fashion only when traversing a prescribed sector including the first angular position. Further, when the prescribed first angular position is reached, a first X ray pulse is generated.

35 Claims, 3 Drawing Sheets

X RAY COMPUTER TOMOGRAPH AND METHOD FOR OPERATING AN X RAY COMPUTER TOMOGRAPH

PRIORITY STATEMENT

The present application hereby claims priority under 35 U.S.C. §119 on German patent application numbers DE 10 2006 003 829.0 filed Jan. 26, 2006, the entire contents of each of which is hereby incorporated herein by reference.

FIELD

Embodiments of the invention generally relate to an X ray computer tomograph and/or a method for operating an X ray computer tomograph.

BACKGROUND

A method is known from U.S. Pat. No. 5,400,378. The first step in reducing the applied X ray dose during a volumetric transirradiation for recording tomograms is to record shadow images or topograms of each slice of a region to be examined, doing so at an angle of 0° to 90°. An optimum X ray dose and the tube current, corresponding thereto, for the respective slice are then calculated therefrom. Subsequently, each slice is transirradiated with the previously determined optimum X ray dose in order to produce tomograms. The tube current is appropriately modulated over the slices to this end. The proposed method requires a two fold scanning of the patient and thus a high time outlay. Irrespective thereof, the patient is already subjected to the load of a relatively high X ray dose as the topograms are being recorded.

DE 10 2004 043 859 A1 discloses a method for controlling the modulation of the tube current by using a single topogram. In this case, the single topogram is evaluated by using previously stored information relating to the attenuation of the X radiation in a direction orthogonal thereto. The tube current is modulated for each slice in order to attain an optimum X ray dose on the basis of the results attained in this case. The proposed method is certainly less time consuming, because of the production of only a single topogram. However, owing to the approximation methods required to calculate the tube current, inaccuracies can occur that can lead to the application of an X ray dose that is not always optimum.

U.S. Pat. No. 6,393,090 B1 describes a method for operating an X ray computer tomograph in the case of which the slices of the region of the patient that is to be examined are transirradiated at two different angles. A topogram with an item of depth information or a 3D topogram is calculated on the basis of the values measured in the process. In order to carry out the method, the X ray source is held at the first angle, and the patient is then moved along the z-axis and repeatedly transirradiated. Subsequently, the X ray source is rotated and held at the second angle. The patient is again moved along the z-axis and repeatedly transirradiated. The known method is likewise time-consuming. Apart from this, artifacts can be caused during the calculation of the topogram by movements of the organs during the time-offset recording of the slices at different angles.

So-called digital X ray tomosynthesis methods are known from James T. Dobbins III and Devon J. Godfrey "Digital x-ray tomosynthesis: current state of the art and clinical potential", Phys. Med. Biol. 48 (2003) R65-R106 and from James T. Dobbins III "Chest Radiography, Pt. 3: Chest Tomosynthesis", http://www.imagingeconomics.com/library/tools/printengine.asp?printArticleID=200505-05. In this case, a region of a body that is to be examined is transirradiated at different angles, a flat detector being used as detector. It is thereby possible, by using suitable algorithms, to produce a tomosynthesis image with a high resolution at a prescribed slice thickness of the body. The method of X ray tomosynthesis can be carried out by using conventional X ray computer tomographs. All that is required to this end is to process the recordings produced at different prescribed angles by using the suitable algorithm to form the tomosynthesis image.

DE 199 25 395 A1 describes a method for operating an X ray computer tomograph. Data obtained during a volumetric transirradiation is extracted in this case in order to produce a topogram. In order to improve the quality of the topogram, the data belonging to a desired projection direction are read out from a number of rows of the detector system and used to reconstruct the topogram. This document makes no statement on setting and/or determining the optimum X ray dose of the radiations used as a function of the respectively transirradiated slices.

EP 0 531 993 B1 describes a method and an apparatus for producing tomograms and topograms by means of an X ray computer tomograph. The patient is transirradiated in a spiral fashion in this case. The measured values obtained during the spiral transirradiation are further processed in order to produce sectional images. At the same time, measured values recorded at a prescribed angle are further processed to form a topogram. Both the sectional image and the topogram are displayed at the same time. A similar method is known from DE 41 03 588 C1. It is proposed in this case that the recording be broken off when a radiologically detected end point is reached.

SUMMARY

At least one embodiment of the invention aims at eliminating at least one disadvantage according to the prior art. One aim for at least one embodiment, in particular, is to specify a method and/or an X ray computer tomograph that facilitates the production of shadow images with a low time outlay and with the application of as, low an X ray dose as possible.

It is provided in accordance with at least one embodiment of the invention that the X ray source is operated in a pulsed fashion only when traversing a prescribed sector $\Delta\phi$ including the first angular position, in that when the prescribed first angular position is reached a first X ray pulse is generated. According to at least one embodiment of the proposed method, the production of shadow images is performed during the continuous spiral scanning movement of the X ray source relative to the body to be examined. It is therefore no longer necessary to move the X ray source into the prescribed first angular position, to hold it there and subsequently to produce the first shadow image. In accordance with the subject matter of at least one embodiment of the proposed method, a first X ray pulse is generated only when the first angular position is reached. The first angular position lies within a sector $\Delta\phi$ that is traversed by the X ray source during each revolution. The applied X ray dose is substantially reduced by respectively generating merely one X ray pulse only within the sector for the purpose of producing shadow images.

According to an advantageous refinement of at least one embodiment of the invention, the sector includes an angle of at most 100°. Within a sector delimited in this way, it is possible to produce shadow images for different control or diagnostic purposes.

According to an advantageous refinement of at least one embodiment, in order to produce a second shadow image at a prescribed second angular position, which differs from the first angular position and is included in the sector $\Delta\phi$, a second X ray pulse is generated when the prescribed second angular position is reached.

In this case, the first and the second angular positions expediently differ from one another by 10° to 100°, preferably 90°. In this case, an X ray dose that is optimum for the respective region of the body to be transirradiated can advantageously be calculated on the basis of the first and the second shadow image in order to produce a sectional image. This enables a tube current used to generate the X radiation to be modulated in accordance with the optimum X ray dose determined, particularly during a volumetric transirradiation following the production of the shadow images. Consequently, the quality of the sectional images produced during the volumetric transirradiation can be improved and the applied X ray dose can simultaneously be reduced.

The temperature in a rotor of a gantry that holds the X ray source and the matrix detector can be kept in a relatively narrow temperature range in that the shadow image(s) are recorded according to at least one embodiment of the invention during the continuous spiral movement of the X ray source relative to the body to be transirradiated. It is possible to avoid temperature fluctuations that cause an undesired drift in an electronics fitted in the rotor.

By using the method according to at least one embodiment of the invention, it is also advantageously possible, in particular, to produce a 3D shadow image comprising depth information on the basis of the first and the second shadow image. In this case, the first and the second angular positions expediently differ from one another by 10° to 30°, preferably 15°. This enables the production of a 3D shadow image with depth information on the basis of conventional stereoscopic methods.

According to a further refinement of at least one embodiment of the invention, it is possible that the first and the second X ray pulse and, at a prescribed third angular position, which differs from the first and second angular position and is included in the sector $\Delta\phi$, a third X ray pulse are generated in order to produce a third shadow image. A depth tomogram can advantageously be produced according to a tomosynthesis method by using the first, second and third shadow image. The applied X ray dose can be kept particularly low in that the X ray pulses required for producing the first, second and third shadow image are generated only within the sector $\Delta\phi$ during continuous operation. Of course, it is also possible for more than three shadow images to be recorded within the sector $\Delta\phi$ in order to produce a depth tomogram according to the tomosynthesis method.

In accordance with at least one embodiment of the present invention, 15 to 80 tomograms are expediently recorded within the sector $\Delta\phi$ and subsequently further processed to form a depth tomogram according to the tomosynthesis method. Carrying out at least one embodiment of the proposed method during continuous operation enables depth tomograms to be produced particularly quickly.

According to a further advantageous refinement of at least one embodiment, a double pulse formed from a high energy pulse and a low energy pulse is generated in each case when the first and/or the second and/or the third angular position is reached. As an alternative thereto, during the traversal of the sector $\Delta\phi$ a high energy pulse is generated as first and/or second and/or third X ray pulse, and during the next subsequent traversal of the sector $\Delta\phi$ a low energy pulse is generated as further first, further second and/or further third X ray pulse. A high energy image can be produced from the high energy data record obtained by using the at least one high energy pulse, and a low energy image can be produced from the low energy data record obtained by using the at least one low energy pulse. It is thereby possible to selectively display tissues of a prescribed determined density. It is thus possible, for example, to produce bone images and, expediently by using suitable subtraction methods, tissue images.

According to a further advantageous refinement of at least one embodiment of the invention—on the one hand—a first voltage and a first exposure time for generating the at least one high energy pulse and—on the other hand—a second voltage and a second exposure time for generating the at least one low energy pulse are selected such that the high energy pulse and the low energy pulse cause approximately the same X ray dose. Consequently, the high energy images and the low energy images can be recorded with substantially the same image quality in conjunction with a lower radiation burden on a patient. The mutual adjustment of two manipulated variables, specifically voltage and exposure time, can be carried out with a low outlay.

According to a further, particularly advantageous refinement of at least one embodiment, a diaphragm downstream of the X ray source in the beam path is opened completely at least during the generation of the X ray pulse. It is thereby possible to project onto the matrix detector a shadow image that extends over its entire row depth in the z-direction. Overlapping shadow images of the region of the body to be examined can therefore be recorded. Particularly exact shadow images can be produced therefrom by means of suitable interpolation methods.

According to a further measure of at least one embodiment of the invention, in the case of an X ray computer tomograph, a pulse generating device for generating a first X ray pulse when the prescribed first angular position is reached is provided and a control device is provided for operating the pulse generating device only during the traversal of the X ray source of a prescribed sector $\Delta\phi$ including the first angular position. The proposed X ray computer tomograph can be used to produce a first shadow image within only one sector $\Delta\phi$ at at least one prescribed angular position by using a first X ray pulse. The applied X ray dose can be substantially reduced in that in order to produce the first shadow image the X ray source remains switched off outside the sector $\Delta\phi$, and is driven in a pulsed fashion within the sector $\Delta\phi$ only when prescribed angular positions are reached.

At the same time, a continuous operation of the X ray computer tomograph is possible in which the X ray source is moved spirally relative to the body to be examined and at high speed. In order to produce a shadow image, it is, in particular, not necessary to stop the X ray source at the prescribed first angular position and subsequently to set it moving again. The proposed continuous operation and the generation of X ray pulses at prescribed angular positions within the sector $\Delta\phi$ enables the X ray computer tomograph to be operated at a constant temperature. Drifting of the electronic components caused by temperature fluctuations is advantageously avoided.

The pulse generating device according to at least one embodiment of the invention can be a conventional device for generating X ray pulses. A pulse width corresponding approximately to an integration time of the matrix detector, for example, is set in this case. Typical pulse widths are in the range from 300 to 600 µs, preferably 400 to 450 µs.

The control device for operating or driving the pulse generating device is usually a computer having a suitable control program. It is thereby possible within the sector $\Delta\phi$ to set the first angular position and, if appropriate, further angular positions at which one or more shadow images are to be produced.

The sector $\Delta\phi$ includes an angle of at most 100°. Shadow images required for determining control parameters and for diagnostic purposes can be produced in such a sector $\Delta\phi$. The applied X ray dose can be substantially reduced in that the X ray source for producing shadow images is not operated at least outside the sector $\Delta\phi$.

According to an advantageous refinement of at least one embodiment, a second X ray pulse for producing a second shadow image can be generated with the control device at a prescribed second angular position, which differs from the first angular position and is included in the sector $\Delta\phi$ when the prescribed second angular position is reached. The first and the second angular positions can differ in this case from one another by 10° to 100°, preferably 90°.

According to a further refinement of at least one embodiment of the invention, a computing device is provided for calculating an X ray dose, optimum for producing a sectional image, for the respectively transirradiated region of the body on the basis of the first and the second shadow image. When, in particular, the first and the second shadow images are recorded at angular positions differing by 90°, it is possible to determine particularly effectively an optimum X ray dose, required for producing a sectional image, for the region to be transirradiated in each case. The computing device can be, in turn, a computer having a suitable program.

According to a further refinement of at least one embodiment, a modulation device is provided for modulating a tube current, used for generating the X radiation, in accordance with the optimum X ray dose determined, during a volumetric transirradiation following the production of the at least one shadow image. The applied X ray dose can be kept at a minimum, and optimum production of images is ensured at the same time with the aid of the proposed modulation device.

According to a further refinement of at least one embodiment, a second imaging device is provided for producing a 3D shadow image including depth information on the basis of the first and the second shadow image. To this end, the first and the second shadow images can be recorded at angular positions that differ from one another by 12° to 20°, preferably 15°. Such a recording enables a stereoscopic projection and thus the production of a 3D shadow image.

According to a further refinement of at least one embodiment, the first and the second X ray pulse and, at a prescribed third angular position, which differs from the first and the second angular position and is included in the sector $\Delta\phi$, a third X ray pulse can be generated with the aid of the control device in order to produce a third shadow image. In this case, a third imaging device can be provided for producing a depth tomogram according to a tomosynthesis method by using the first, second and third shadow image.

According to a further refinement of at least one embodiment of the invention, a device is provided for generating a double pulse formed from a high energy pulse and a low energy pulse such that a double pulse is generated in each case when the first and/or second and/or third angular position is reached. Alternatively, a device can be provided for alternately generating at least one high energy pulse and at least one low energy pulse during the traversal of the sector $\Delta\phi$ a high energy pulse is generated as first and/or second and/or third X ray pulse, and during the next subsequent traversal of the sector $\Delta\phi$ a low energy pulse is generated as further first, further second and/or further third X ray pulse.

Furthermore, a fourth imaging device is provided in at least one embodiment, for producing a high energy image from the high energy data record obtained with the at least one high energy pulse, and for producing a low energy image from the low energy data record obtained with the at least one low energy pulse. Body sections with a high density, for example, bone or the like, can be displayed particularly exactly with the aid of the high energy data record. In particular, the low energy data record can be used to display body sections with a low density, for example soft parts, organs and the like. The resolution of the X ray images produced by using different energies can be further improved by appropriate subtraction methods.

According to a further advantageous refinement of at least one embodiment—on the one hand—a setting device is provided for setting a first voltage and a first exposure time for generating the at least one high energy pulse, and—on the other hand—for setting a second voltage and a second exposure time for generating the at least one low energy pulse, this being done in such a way that the high energy pulse and the low energy pulse cause approximately the same X ray dose. The X ray source can be switched over from high energy operation to low energy operation outside the sector $\Delta\phi$ in particular. This also enables the use of X ray sources with a relatively sluggish switchover behavior.

According to a particularly advantageous further refinement of at least one embodiment of the invention, the control device can be used to drive a diaphragm downstream of the X ray source in the beam path in such a way that the diaphragm is automatically opened completely during the generation of the X ray pulse. Consequently, an X ray fan emitted by the X ray source opens in the z-direction so wide that the matrix detector is irradiated over its entire row depth extending in the z-direction. It is thereby possible to produce shadow images with a maximum extent in the z-direction.

The image producing devices and the control device in at least one embodiment can, in turn, expediently be a computer that is provided with suitable programs for producing images and for controlling the diaphragm.

BRIEF DESCRIPTION OF THE DRAWINGS

Example embodiments of the invention are explained in more detail below with the aid of the drawings, in which.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
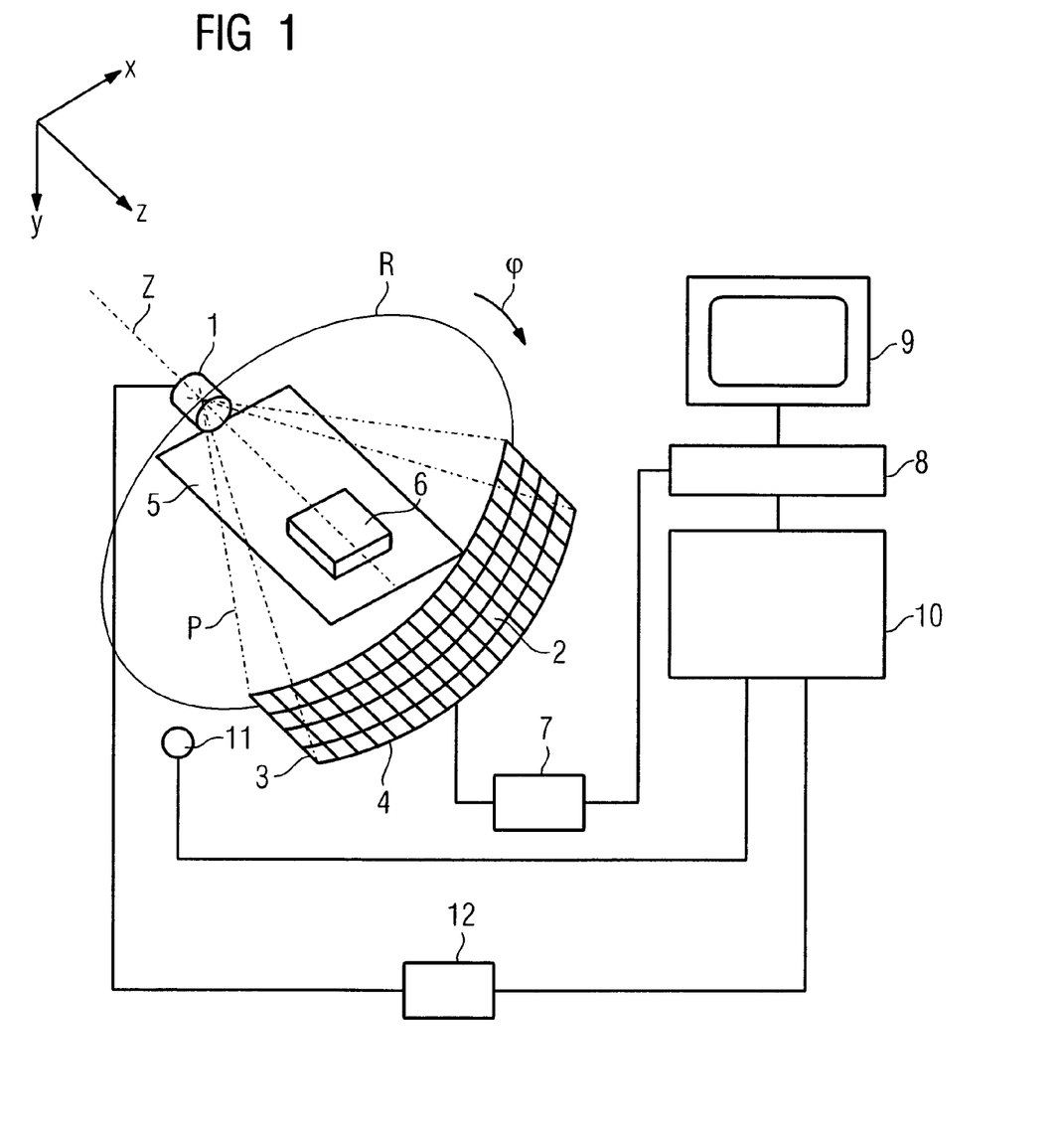
FIG. 1 shows a schematic of the mode of operation of an X ray computer tomograph.

In FIG. 1, an X ray source 1 and a matrix detector 2 are fitted in an opposing arrangement on a rotor R, that can rotate about a z-axis Z, of a gantry (not shown here). The matrix detector 2 comprises a number of rows 3 extending in the rotation direction f, each of the rows 3 consisting of a multiplicity of juxtaposed detector elements 4. A depth of the matrix detector 2, which is formed by the rows 3 juxtaposed in the z-direction, is also denoted as row depth in conjunction with an embodiment of the present invention.

Arranged inside the rotor R parallel to the z-axis Z is a continuously movable patient table 5 on which a body 6 to be examined, for example the body of a patient is held. An evaluation electronics 7 downstream of the matrix detector 2 is connected to a computer 8. Further connected to the computer 8 are a display screen 9 and an input device (not illustrated here in more detail), for example a keyboard and/or a mouse. Moreover, the computer 8 comprises a control device 10 that is connected to a sensor 11 for detecting the respective angular position of the X ray source 1, and to a pulse generating device 12 for generating high voltage pulses.

The function of the X ray computer tomograph shown in FIG. 1 will now be explained in more detail with additional reference to FIGS. 2 to 5.

Figure 2:
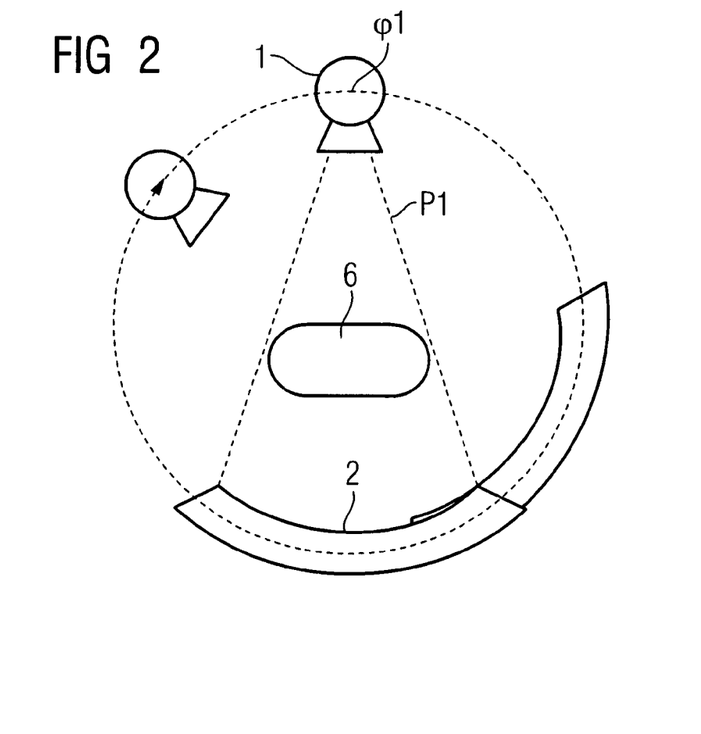
FIG. 2 shows a schematic view of the measuring arrangement during the recording of a shadow image.

In order to produce a single shadow image or topogram, the first step is to transmit the desired angular position f1 to a control program provided on the computer 8. The control program is used to trigger the rotation of the rotor R, the driving of the pulse generating device 12 for generating high voltage pulses, and the evaluation electronics 7, particularly by using the signals supplied by the sensor 11, doing so such that when the prescribed first angular position f1 of the X ray source 1 is reached, a high voltage pulse is generated automatically by way of the pulse generating device 12, and thus an X ray pulse P1 is generated with the aid of the X ray source 1. A shadow image detected with the matrix detector 2 is digitized by way of the evaluation device 7. The data record produced in this case is transmitted to a first image evaluation program that is likewise provided on the computer 8. With the aid of the first image evaluation program, the sequentially recorded shadow images, which partially overlap in the z-direction, are processed to form an overall shadow image by using conventional algorithms.

Figure 3:
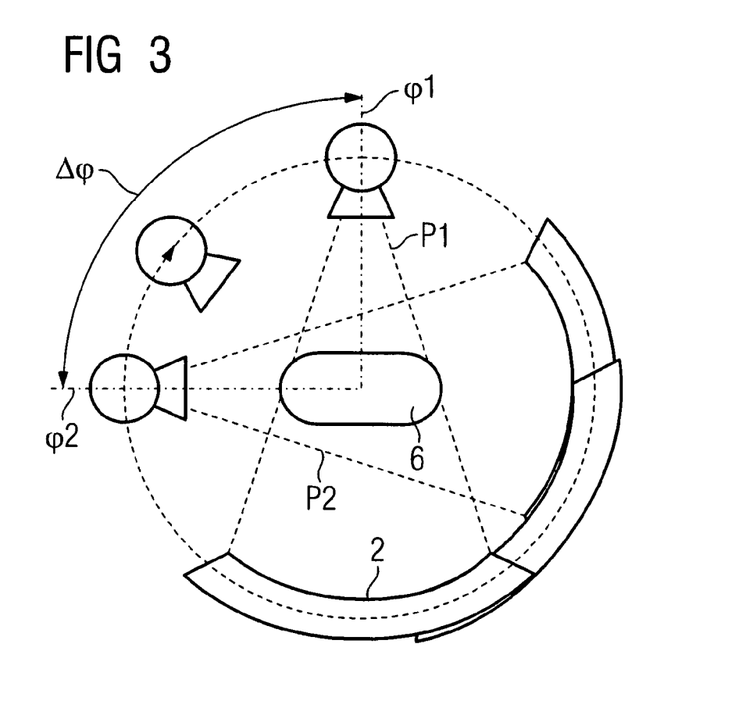
FIG. 3 shows a schematic view of the measuring arrangement during the recording of two shadow images for determining an optimum X ray dose.

FIG. 3 shows a variant of the method according to an embodiment of the invention. Accordingly, within a sector $\Delta\phi$ of 90° in this case a first shadow image is recorded at a prescribed first angular position f1 by generating a first X ray pulse P1, and a second shadow image is recorded at a second angular position f2, differing therefrom by 90°, by generating a second X ray pulse P2. According to conventional methods, an optimum X ray dose for the transirradiation of the respective region of the body 6 is calculated from the two shadow images in order to produce sectional images. In accordance with the calculated optimum X ray doses, during a subsequent volumetric transirradiation for producing sectional images a tube current corresponding thereto is appropriately modulated in the z-direction as a function of a position of the X ray source 1. It is thereby possible to achieve a particularly good quality of the tomograms produced, and at the same time to keep the applied X ray dose to a minimum.

Figure 4:
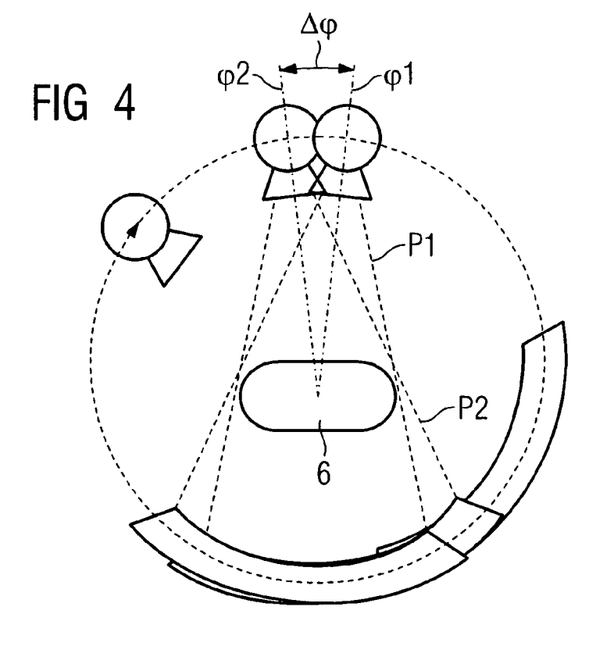
FIG. 4 shows a schematic view of the measuring arrangement during the recording of two sectional images for producing a stereoscopic 3D sectional image.

FIG. 4 shows a further variant of the method according to an embodiment of the invention. Here, within a sector $\Delta\phi$ of 10° to 20°, preferably 15°, once again a first shadow image is recorded at a first angular position f1, and a second shadow image is recorded at a second angular position f2. The sector $\Delta\phi$ in which the two angular positions f1, f2 lie is here at most 20°.

According to the principle of stereoscopy, shadow images recorded at such angular positions f1, f2 are suitable for producing 3D shadow images according to conventional methods. 3D shadow images advantageously comprise depth information. The applied X ray dose can be kept particularly low in that here, as well, in each case only one first P1 and one second X ray pulse P2 are generated within the sector $\Delta\phi$ in accordance with the method according to an embodiment of the invention. The X ray pulses P1, P2 are generated during the continuous rotation of the rotor R and the continuous movement of the body 6 in the z-direction. The method is particularly time saving.

Figure 5:
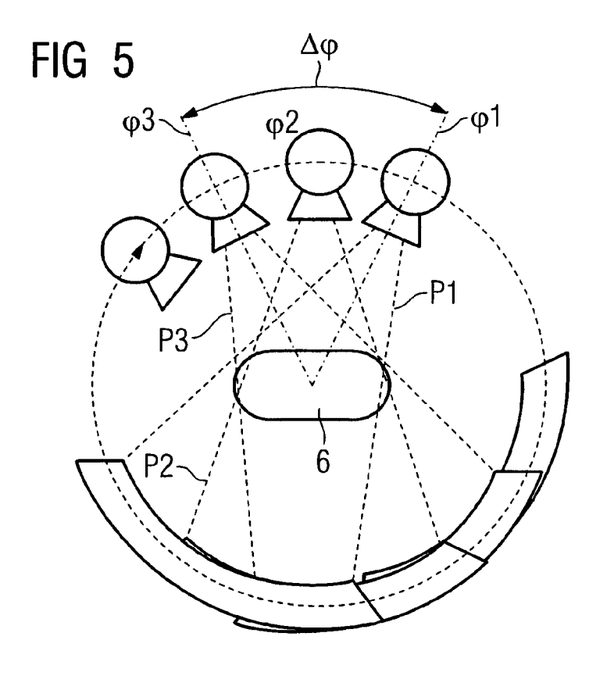
FIG. 5 shows a schematic view of the measuring arrangement during the recording of three sectional images for producing a depth tomogram.

FIG. 5 shows a further variant of the method according to an embodiment of the invention. In this case, within a sector $\Delta\phi$ of approximately 50° a first shadow image is recorded at a first angular position f1, a second shadow image at a second angular position f2, and a third shadow image at a third angular position f3. The first f1, the second f2 and the third angular position f3 differ from one another approximately by 25° in each case. A depth tomogram can be produced using a conventional tomosynthesis method by way of first, second and third shadow images recorded in such a way at different angular positions. In this case, as well, a short X ray pulse P1, P2, P3 with a pulse width of 430 µs, for example, is generated only within a relatively small sector Δφ of less than 80°, preferably less than 60°, in order to produce each of the tomograms. The tomograms are produced, in turn, as the X ray source 1 moves in a spiral fashion relative to the body 6. Of course, in order to produce particularly accurate depth tomograms according to the tomosynthesis method, it is also possible to record not only three tomograms, but, for example 15 to 80 tomograms within the sector Δφ, of 10°-30°, for example, preferably 20°, doing so in each case by using X ray pulses, and subsequently to process these further as appropriate. The applied dose can nevertheless be kept low in that also only X ray pulses are used to record a relatively large number of tomograms.

In the method according to an embodiment of the invention, an X ray pulse P1, P2, P3 and, consequently, a shadow image are expediently produced upon each revolution when the respective angular position(s) f1, f2, f3 are respectively reached. According to an advantageous refinement, it is possible that after the sector Δφ has been traversed in each case a voltage of the tubes and an exposure time are changed by means of an actuating device (not shown here) upstream of the pulse generating device 12 such that in conjunction with a substantially constant X ray dose the energy of the X ray pulses P1, P2, P3 is changed in an alternating fashion. For example, it is possible firstly to generate high energy X ray pulses during one revolution, and to generate low energy pulses during the revolution following next, etc.

The switchover between high and low energy pulses can advantageously already be performed when the X ray source 1 has left the sector Δφ. This also enables the use of conventional relatively sluggish X ray sources 1 or setting devices. Additional information, in particular relating to the structure of a transirradiated tissue, bone or the like, can be obtained with the aid of the proposed alternating production of shadow images by way of high and low energy pulses. Conventional imaging methods can be used to produce appropriately differentiated images.

In order to produce a single shadow image, a 3D shadow image or a depth tomogram according to the tomosynthesis method, it is possible to provide the computer 8 with imaging devices and programs with the aid of which the shadow images produced can be appropriately processed according to conventional methods.

According to an advantageous refinement of an embodiment of the invention, a diaphragm (not shown here) downstream of the X ray source 1 is automatically opened to a maximum by way of the control program provided in the computer 8 upon selection of a function for carrying out the method according to an embodiment of the invention, that is to say for producing shadow images, such that X radiation is applied to the complete row depth of the matrix detector 2 with the aid of the X ray pulse P generated. This enables the production of overlapping tomograms at each of the angular positions f1, f2 or f3. The overlapping tomograms can be corrected by way of suitable methods, for example interpolations, and it is possible thereby to produce particularly exact overall shadow images.

Of course, the method according to an embodiment of the invention can also be applied in the case of X ray computer tomographs on whose rotor R there are fitted in an opposing arrangement not only an X ray source 1 and a matrix detector 2, but, for example in an arrangement perpendicular thereto, a further X ray source and, in an opposing arrangement, a further matrix detector.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a first shadow image with the aid of an X ray computer tomograph at a prescribed first angular position, comprising:

continuously rotating an X ray source, rotatable about a z-axis, together with a matrix detector fitted in an opposing arrangement about a body that is continuously moved in a direction parallel to the z-axis in order to generate a spiral movement relative to the body;

transirradiating the body with X radiation at a prescribed first angular position of the X ray source, and as a consequence thereof, converting signals detected by the matrix detector into a data record corresponding thereto; and producing the first shadow image using at least one such data record, the shadow image being produced during the continuous spiral scanning movement of the X ray source relative to the body to be examined, the X ray source being operated during each revolution of the continuous spiral movement in a pulsed fashion only when traversing a prescribed sector including the first angular position, wherein, when the prescribed first angular position is reached, a first X ray pulse is generated for producing the first shadow image and remains switched off outside the sector.

2. The method as claimed in claim 1, wherein the sector includes an angle of at most 100°.

3. The method as claimed in claim 1, wherein, in order to produce a second shadow image at a prescribed second angular position, which differs from the first angular position and is included in the sector, a second X ray pulse is generated when the prescribed second angular position is reached.

4. The method as claimed in claim 3, wherein the first and the second angular position differ from one another by 10° to 100°.

5. The method as claimed in claim 3, wherein an X ray dose that is optimum for the respectively transirradiated region of the body is calculated on the basis of the first and the second shadow image in order to produce a sectional image.

6. The method as claimed in claim 5, wherein, during a volumetric transirradiation following the production of the shadow images, a tube current used to generate the X ray beams is modulated in accordance with the optimum X ray dose determined.

7. The method as claimed in claim 3, wherein a 3D shadow image comprising depth information is produced on the basis of the first and the second shadow image.

8. The method as claimed in claim 3, wherein the first and the second X ray pulse and, at a prescribed third angular position, differs from the first and second angular position and is included in the sector, a third X ray pulse are generated in order to produce a third shadow image.

9. The method as claimed in claim 8, wherein a depth tomogram is produced according to a tomosynthesis method by using the first, second and third shadow image.

10. The method as claimed in claim 8, wherein a double pulse formed from a high energy pulse and a low energy pulse is generated in each case when at least one of the first, the second and the third angular position is reached.

11. The method as claimed in claim 8, wherein, during the traversal of the sector, the high energy pulse is generated as at least one of the first, second and third X ray pulse, and during the next subsequent traversal of the sector, the low energy pulse is generated as at least one of a further first, a further second and a further third X ray pulse.

12. The method as claimed in claim 10, wherein a high energy image is produced from the high energy data record obtained by using the at least one high energy pulse, and a low energy image is produced from the low energy data record obtained by using the at least one low energy pulse.

13. The method as claimed in claim 10, wherein a first voltage and a first exposure time for generating the at least one high energy pulse and a second voltage and a second exposure time for generating the at least one low energy pulse are selected such that the high energy pulse and the low energy pulse cause approximately the same X ray dose.

14. The method as claimed in claim 1, wherein a diaphragm downstream of the X ray source in the beam path is opened completely at least during the generation of the X ray pulse.

15. An X ray computer tomograph, comprising:
a gantry, on whose rotor, rotatable about a z-axis, there are fitted an X ray source and, in an opposing arrangement, a matrix detector;
a movement device for continuously moving a body to be examined inside the gantry in a direction parallel to the z-axis such that a spiral movement relative to the body is executable with the X ray source, and the body is transirradiatable with X radiation at a prescribed first angular position of the X ray source;
a conversion device to convert the signals detected by the matrix detector at the first angular position into a data record corresponding thereto;
a first imaging device to produce a first shadow image by using at least one such data record;
a pulse generating device to generate a first X ray pulse for producing the first shadow image when the prescribed first angular position is reached, the shadow image being produced during the continuous spiral scanning movement of the X ray source relative to the body to be examined; and
a control device to operate the pulse generating device only during each revolution of the spiral movement of the X ray source of a prescribed sector including the first angular position, and to switch off the X ray source outside the sector.

16. The X ray computer tomograph as claimed in claim 15, wherein the sector Δφ comprises an angle of at most 100°.

17. The X ray computer tomograph as claimed in claim 15, wherein a second X ray pulse to produce a second shadow image is generatable with the control device at a prescribed second angular position, which differs from the first angular position and is included in the sector when the prescribed second angular position is reached.

18. The X ray computer tomograph as claimed in claim 17, wherein the first and the second angular position differ from one another by 10° to 100°.

19. The X ray computer tomograph as claimed in claim 17, further comprising:
a computing device to calculate an X ray dose, optimum for producing a sectional image, for the respectively transirradiated region of the body on the basis of the first and the second shadow image.

20. The X ray computer tomograph as claimed in claim 19, further comprising:
a modulation device to modulate a tube current, used for generating the X ray beams, in accordance with the optimum X ray dose determined, during a volumetric transirradiatlon following the production of the at least one shadow image.

21. The X ray computer tomograph as claimed in claim 17, further comprising:
a second imaging device to produce a 3D shadow image comprising depth information on the basis of the first and the second shadow image.

22. The X ray computer tomograph as claimed in one claim 17, wherein the first and the second X ray pulse and, at a prescribed third angular position, which differs from the first and second angular position and is included in the sector, a third X ray pulse are generatable with the aid of the control device in order to produce a third shadow image.

23. The X ray computer tomograph as claimed in claim 22, further comprising:
a third imaging device to produce a depth tomogram according to a tomosynthesis method by using the first, second and third shadow image.

24. The X ray computer tomograph as claimed in claim 22, further comprising:
a device to generate a double pulse formed from a high energy pulse and a low energy pulse such that a double pulse is generated in each case when at least one of the first, second and third angular position is reached.

25. The X ray computer tomograph as claimed In claim 22, further comprising:
a device to alternately generate at least one high energy pulse and at least one low energy pulse such that during the traversal of the sector a high energy pulse is generated as at least one of the first, second and third X ray pulse, and during the next subsequent traversal of the sector a low energy pulse is generated as at least one of a further first, a further second and a further third X ray pulse.

26. The X ray computer tomograph as claimed in claim 24, further comprising:
a fourth imaging device to produce a high energy image from the high energy data record obtained with the at least one high energy pulse, and to produce a low energy image from the low energy data record obtained with the at least one low energy pulse.

27. The X ray computer tomograph as claimed in claim 24, wherein a setting device is provided to set a first voltage and a first exposure time to generate the at least one high energy pulse, and to set a second voltage and a second exposure time to generate the at least one low energy pulse, this being done in such a way that the high energy pulse and the low energy pulse cause approximately the same X ray dose.

28. The X ray computer tomograph as claimed in claim 15, wherein the control device is usable to drive a diaphragm downstream of the X ray source in the beam path in such a way that the diaphragm is automatically opened completely during the generation of the X ray pulse.

29. The method as claimed in claim 3, wherein the first and the second angular position differ from one another by 90°.

30. The method as claimed in claim 4, wherein an X ray dose that is optimum for the respectively transirradiated region of the body is calculated on the basis of the first and the second shadow image in order to produce a sectional image.

31. The method as claimed in claim 9, wherein a double pulse formed from a high energy pulse and a low energy pulse is generated in each case when at least one of the first, the second and the third angular position is reached.

32. The method as claimed in claim 9, wherein, during the traversal of the sector, the high energy pulse is generated as at least one of the first, second and third X ray pulse, and during the next subsequent traversal of the sector, the low energy pulse is generated as at least one of a further first, a further second and a further third X ray pulse.

33. The method as claimed in claim 11, wherein a high energy image is produced from the high energy data record obtained by using the at least one high energy pulse, and a low energy image is produced from the low energy data record obtained by using the at least one low energy pulse.

34. The method as claimed in claim 11, wherein a first voltage and a first exposure time for generating the at least one high energy pulse and a second voltage and a second exposure time for generating the at least one low energy pulse are selected such that the high energy pulse and the low energy pulse cause approximately the same X ray dose.

35. The X ray computer tomograph as claimed in claim 18, wherein the first and the second angular position differ from one another by 90°.

* * * * *